United States Patent [19]

Marihart

[11] Patent Number: 4,698,090
[45] Date of Patent: Oct. 6, 1987

[54] PROCESS FOR PREPARATION OF COMPOSITIONS FOR MODIFYING PLANT GROWTH; COMPOSITIONS FOR PLANT GROWTH MODIFICATION; AND METHOD FOR THE USE THEREOF

[75] Inventor: John R. Marihart, Fresno, Calif.

[73] Assignee: Pacific Micro Minerals, Inc., Fresno, Calif.

[21] Appl. No.: 771,554

[22] Filed: Aug. 30, 1985

Related U.S. Application Data

[63] Continuation-in-part of Ser. No. 609,778, May 14, 1984, abandoned.

[51] Int. Cl.$^4$ ............................................. C05F 11/02
[52] U.S. Cl. .................................... 71/24; 71/DIG. 2
[58] Field of Search .............................. 71/24, DIG. 2

[56] References Cited

U.S. PATENT DOCUMENTS 4,425,149  1/1984  Kimbro ................................... 71/24

OTHER PUBLICATIONS

CA 80:23447s, "Auxin-Like . . . Leonardite", 1973, O'Donnell.
CA 78:14965r, "Extraction of . . . Resin", 1972, Ortiz et al.

Primary Examiner—Ferris H. Lander
Attorney, Agent, or Firm—Townsend and Townsend

[57] ABSTRACT

A process for the preparation of compositions for modifying plant growth including extracting humic acids by the reacting of organic chelating agents with leonardite ore; compositions produced by such process; and methods for use thereof for modifying plant growth and fruiting.

24 Claims, No Drawings

PROCESS FOR PREPARATION OF COMPOSITIONS FOR MODIFYING PLANT GROWTH; COMPOSITIONS FOR PLANT GROWTH MODIFICATION; AND METHOD FOR THE USE THEREOF

BACKGROUND OF THE INVENTION

This is a continuation-in-part of U.S. patent application Ser. No. 609,778, filed May 14, 1984 now abandoned.

1. Field of the Invention

The present invention relates to novel processes for the preparation of compositions for modifying plant vegetative growth and fruiting, and to the compositions produced by such processes. The present invention further relates to the method for the use of the compositions in stimulating the growth of plants. The present invention more particularly relates to processes for preparing aqueous humic acid based compositions from leonardite ore, the humic based compositions prepared thereby, and the use of such compositions to modifying vegetative growth and fruiting of the plants to which they are applied.

2. Description of the Prior Art

Leonardite ores have long been known to be sources of organic materials adapted for use as soil and foliar additives having application in the regulation of plant growth. In particular, leonardite ore is recognized as a primary source for a wide variety of humates and humic acids. A wide variety of processes have been proposed for the extraction of the humic fractions from leonardite ore for use of the compositions so extracted in treating plants to modify plant vegetative growth and fruiting and the uptake of nutrients by plants so treated.

Leonardite ore is believed to be an oxidized form of lignite ore, which is, in effect, a precursor to leonardite ore in the biochemical and chemical pathways of natural leonardite synthesis. Hence, it is recognized that any mined sample of leonardite ore-bearing earth is expected to contain at least some lignite ore, as well as a plurality of organic and inorganic impurities. Accordingly, as used herethroughout, the term "leonardite ore" will be understood as referring to ore samples inclusive of lignite as well.

Further, it is understood that many known processes for extracting humic acids and humates from leonardite ore actually result in the extraction of fulvic and phenol carboxylic fractions as well. It is, accordingly, to be recognized that the term "humic acid", as used herein, is not intended to be construed as excluding the possibility of the presence of fulvic acids and phenol carboxylic acids in fractions and compositions extracted and produced by known processes or the processes of the present invention.

While many of the humic acid products prepared using known techniques of extraction from leonardite ore have been effective to one degree or another in stimulating plant growth when applied thereto, the response of various plants to the application thereon of such compositions has proven to be inconsistent. Further, some known processes for extracting humic acid products and compositions from leonardite ore result in the production of compositions having limited stability against degradation and consequently having limited shelf lives whereby storage thereof for protracted periods prior to application to plants and soils results in a significant diminishment of the effectiveness of the composition.

Moreover, few such compositions prepared by known processes have been known to effectively increase both vegetative growth and fruiting in a variety of plants and most of such beneficial effects obtained by applying compositions prepared conventionally have been inconsistent and ephemeral.

Therefore, it has long been known that it would be desirable to have a process for extracting humic acids from leonardite ore which would result in the preparation of a product or composition which is capable of being stored for protracted periods of time without substantial degradation thereof or diminishment of the effectiveness thereof for use in stimulating and regulating plant growth. Further, it has been recognized that there is a need in agriculture for such products and preparations, the use of which is capable of increasing both the vegetative growth of plants on which it is applied, as well as the fruiting thereof. Moreover, it has long been known that it would be desirable to have such a product and a method for the use thereof which finds application in modifying the vegetative growth and fruiting of a wide variety of crops with substantially consistent and repeatable results in a wide variety of ecological conditions

OBJECTS AND SUMMARY OF THE INVENTION

Therefore, it is an object of the present invention to provide improved processes for extracting humic acids from leonardite ore.

Another object is to provide such processes having a minimum of steps and which is capable of utilizing readily available apparatuses and materials.

Another object is to provide such processes which are capable of reliably and consistently producing compositions having high stability against degradation and which are capable of being stored for protracted periods of time without degradation thereof.

Another object is to provide improved plant growth modifying compositions capable of modifying the vegetative growth and fruiting of plants on which they are applied.

Another object is to provide such plant growth modifiers and a method for the use thereof which can be employed dependably and in a manner fully compatible with other agricultural and manufacturing practices.

Another object is to provide such plant growth modifiers and method which are well suited for use on a wide variety of annual and perennial plants and which are particularly well suited for use on cotton, grape, olive and tomato plants.

Another object is to provide such plant growth modifiers and method which can be employed in conjunction with conventional fertilizers, growth regulators, and equipment for the application thereof without diminishment of the beneficial effects of either the plant growth modifiers and method of the present invention, or that of the conventional plant growth regulators, fertilizers, or methods.

These and other objects and advantages will become apparent by reference to the accompanying descriptions.

DESCRIPTION OF THE PREFERRED EMBODIMENT

I. Processes for Preparing Plant Growth Stimulating Compositions and Products Prepared Thereby The processes of the present invention are adapted for use in the extraction of a variety of humic acids and humic acid derivatives by the reaction of organic chelating agents with leonardite ore. Preferably, leonardite ore having a relatively high humic acid content, such as that commonly mined in North Dakota having humic acid contents as high as 80% by weight, is used in practicing the process of the present invention. However, inasmuch as the processes herein described are believed to extract a fairly specific spectrum or fraction of humic acids out of the overall number of humic acids present in the leonardite ore, comprising perhaps as little as 8 to 10% by weight of the total humic acid content of the ore, it will be recognized that the percentage by weight of humic acids in a given ore sample, and the origin of the ore sample, are not to be considered controlling for limiting in the practice of the described processes.

An important feature of the processes of the present invention resides in the discovery that organic chelating agents are useful in the extraction of fractions of the overall number of humic acids present in the leonardite ore. In accordance with the present invention, leonardite ore, preferably crushed prior to the use thereof, is reacted in a heated aqueous medium in the presence of one or more organic chelating agents. Preferably the aqueous medium is heated prior to the introduction of the reactants.

Representative of the organic chelating agents adapted for use in carrying out the processes of the present invention are the following:

The group consisting of the ammonium salts and metal salts of gluconic acid, glucoheptoic acid, citric acid, tartaric acid, tartronic acid, galactaric acid, glucaric acid, glutaric acid, and glutamic acid, such metal salts including the sodium, potassium, copper, iron, magnesium, manganese, zinc, calcium, lithium, rubidium and cesium salts of such acids;

the group consisting of sodium glucamine, potassium glucamine, ammonium glucamine, copper glucamine, ferrous glucamine, magnesium glucamine, manganese glucamine, zinc glucamine, calcium glucamine, lithium glucamine, rubidium glucamine and cesium glucamine; and the group of what are commonly referred to as "synthetic" organic chelating agents, and more particularly the group consisting of amino acid chelating agents representative of which are ethylene diamine tetraacetic acid (hereinafter referred to as "EDTA"), hydroxyethylene diamine triacetic acid (hereinafter referred to as "HEDTA"), diethylene triamine pentaacetic acid (hereinafter referred to as "DTPA"), nitrilo triacetic acid (hereinafter referred to as "NTA"), and ethanol diglycine, as well as the ammonium salts and metal salts thereof, most particularly the sodium salts.

An important aspect of the present invention resides in the surprising and unexpected production of stable yet effective compositions for modifying plant growth, regardless of the organic chelating agent or agents chosen. Further, experimentation has shown that the compositions of the present invention surprisingly produce a hormonal or simulated hormonal response in plants on which they are applied. Such response is believed related to the nature of the humic acid fractions extracted from the leonardite ore by the processes of the present invention or to the resultant reaction products, although the exact make-up and structure of the compositions produced by the disclosed processes have as yet resisted analysis.

The organic chelating agents serve as reactants and, possibly, as means for limiting the potentially deleterious effects of the presence of otherwise free metal ions in the resulting composition.

Preferably, although not necessarily, the organic chelating agent or agents chosen are water soluble.

In a modified form of the described process, the pH of the resultant aqueous composition of extracted humic acid derivatives is then adjusted to stabilize the composition against degradation and to provide a prolonged potential shelf life. In a further modified form of the process of the present invention, the composition derived by the reaction of leonardite ore with one or more organic chelating agents is blended with a humic acid composition prepared by the reaction of leonardite ore with potassium hydroxide or sodium hydroxide. In still a further modification of the subject process, the composition is enhanced as to nutritive value by the introduction of nitrogen, phosphorous, potassium and other nutrients.

In order to disclose the processes of the subject invention still more clearly, attention is invited to the following illustrative examples. It is understood, however, that these examples are merely illustrative and that the subject invention is not to be limited to the specific conditions or details set forth. In the following examples, all parts are by weight, unless otherwise indicated.

EXAMPLE I 9 parts (by weight) of leonardite ore is introduced into 75 parts water previously heated, preferably, to a temperature in a range of about 170° F. (77° C.) to 190° F. (88° C.), but not exceeding 225° F. (107° C.). 15 total parts by weight of sodium gluconate, the sodium salt of gluconic acid, is then added and the resultant mixture is mixed for 5 hours to permit complete reaction. After mixing, the mixture is pumped to a settling tank for 24 hours to 7 days to separate into liquid and solid phases, after which the supernatant, partially separated liquid phase, containing the subject composition, is pumped to standard cone tanks for 3 to 7 days for further settling. The settled liquid composition is pumped to a mixer and adjusted therein to a pH of 12.5 or higher by the addition of concentrated sodium hydroxide or potassium hydroxide The resultant aqueous composition is then adapted to be stored for periods of at least one year prior to use thereof without significant degradation or loss of effectiveness. Optionally, the composition can be used at extracted pH range which can vary from 4.5 to 6.5, depending upon the chelating agent used.

EXAMPLE II

The process described in Example I is repeated and the resultant composition, hereinafter designated as "Composition A", is mixed with a liquid composition, hereinafter designated as "Composition B", produced by the process described immediately below.

In preparing Composition B, about 72 to 74 parts (by weight) of water is heated to at least 180° F. (82° C.). Preferably, the water temperature is about 200° F. (93° C.). About 20 to 22 parts of leonardite ore is added to the water and blended for about ½ hour. 5 parts of potassium hydroxide or sodium hydroxide is added to the water to raise the pH to about 11.00, and mixed for a period of about 2 to 5 hours. Thereafter, one part of hydrogen peroxide is added. The liquid composition is permitted to settle, and excess solid matter is removed.

About 50 parts of Composition B are added to about 12.5 parts of Composition A in about 37.5 parts of water. The resultant mixture is mixed or blended for a period sufficient to produce a substantially homogeneous mixture. The pH is adjusted to about 12.0 by the addition of sodium hydroxide or potassium hydroxide. The mixture, hereinafter designated as "Composition C", is again blended to ensure homogeneity.

It is believed that the presence of positive ions and ammonia are detrimental to the effects of the resultant composition on plant growth, and more particularly on plant fruitage, and therefore it is important that care be taken in the preparation and use of the composition produced by the process of this example to avoid the introduction of ammonia or dissociable metal salts into the mixture.

EXAMPLE III

About 14 parts of Composition A, 9 parts of Composition B, 33.1 parts of phosphoric acid, 11.9 parts potassium hydroxide, 6.2 parts of ammonia, 18.3 parts of water, 3.6 parts of zinc, 2.5 parts of iron, and 1.4 parts of manganese are mixed to produce a composition, hereinafter designated as "Composition D", having as active ingredients humic acids, potassium phosphate, ammonium phosphate and the aforementioned minor nutrients. The resultant composition is one having a positive effect on the rate of vegetative growth and fruiting of plants to which it is applied and which also provides essential nitrogen, phosphorous and potassium nutrients, the need for which increases with the accelerated growth. In particular, Composition D provides relatively high levels of phosphates which are essential to plants during fruiting.

The foregoing examples are illustrative of the processes of the present invention capable of producing compositions having beneficial effects on plant vegetative growth and fruiting and the percentages of the reactants used are representative rather than controlling.

II. Method for Use of Plant Growth Stimulating Compositions

In accordance with the subject invention, plants are treated with single or multiple applications of an effective amount of the plant growth modifying compositions produced by the processes hereof diluted as necessary for selected rates of application thereof. In general, the compositions are most effective if applied on annual crops prior to irrigation or prior to or simultaneously with bloom initiation. On perennial crops, the compositions are best applied immediately prior to or after harvest or, during dormancy, at least one month before the plant enters a vegetative cycle. Soil or foliar applications are effective. As described previously, the effect of the compositions on the growth of plants on which they are applied is, in many cases, hormonal or pseudo-hormonal in nature.

The compositions produced by the processes of the present invention have been found to be unexpectedly compatible with and complementary to many fertilizers as well as growth regulators which are adapted to restrict growth. In particular, the compositions have been discovered to be useful in combination with the growth regulator sold as a water-soluble compositions under the trademark "PIX", containing on a weight basis approximately 4.2% N,N-dimethyly piperidinium chloride and approximately 95.8% inert ingredients (hereinafter referred to as "PIX"); and with the compound 2-Chloroethyl trimethyl ammonium chloride, known variously as "Cycocel" or "chlormequat".

The compositions produce noticeable and consistent increases in vegetative and fruiting growth on a wide variety of plants, particularly when applied at a stress point in the crop cycle and more particularly at such stress times as the harvest period and those relating to the watering of the plants, although the timing of applications relating to water-stress periods in the plants' growth cycle is not believed as critical for perennial crops as for annual crops. However, if the compositions are applied to plants which are in a vegetative state, the results of such application will be minimally effective or inconsistent.

In order to disclose the method of the subject invention still more clearly, attention is invited to the following illustrative examples. It is understood, of course, that these examples are merely illustrative and that the invention is not to be limited to the specific conditions or details set forth. In the following examples, all parts are by weight unless otherwise indicated.

EXAMPLE I

Effects of the composition designated as Composition D on cotton plants growing in California were experimentally determined and the results are summarized in Table 1 below. The cotton, which was of a variety commercially denominated as "SJ2", was grown on 30-inch beds in soil having a type characterized as "oxalis silty clay" with a pH in the range of from 7.6 to 7.7 to a depth of one foot.

The test was conducted in three trials denominated Trials 1, 2 and 3, respectively, and the trials were compared against a fourth trial denominated Trial 4, which served as a control. The cotton fields in which the cotton was grown were divided into plots.

TABLE 1

| TRIAL | RATE OF APPLICATION OF COMPOUND D/TIMING OF APPLICATION | RATE OF APPLICATION OF PIX/TIMING OF APPLICATION | REPLICATION - YIELD (LB/PLOT) | % OF YIELD OF CONTROL |
|---|---|---|---|---|
| 1 | 3 Quarts/Acre 10 days before Bloom (July 7) | 0.5 Pints/Acre 30% Bloom (July 23) | 1 - 2100<br>2 - 1960<br>3 - 1720<br>4 - 1900<br>Avg. - 1920 | 107% |
| 2 | 3 Quarts/Acre First Bloom (July 15) | ⅜ Pints/Acre First Bloom (July 15) | 1 - 2090<br>2 - 1740<br>3 - 1990<br>4 - 1810<br>Avg. - 1908 | 106% |

TABLE 1-continued

| TRIAL | RATE OF APPLICATION OF COMPOUND D/TIMING OF APPLICATION | RATE OF APPLICATION OF PIX/TIMING OF APPLICATION | REPLICATION - YIELD (LB/PLOT) | % OF YIELD OF CONTROL |
| --- | --- | --- | --- | --- |
| 3 | 3 Quarts/Acre<br>First Bloom<br>(July 15) | ½ Pint/Acre<br>Full Bloom<br>(July 23) | 1 - 1920<br>2 - 2010<br>3 - 2000<br>4 - 2110<br>Avg. - 2010 | 112% |
| 4 (Control) | 0 | 0 | 1 - 1840<br>2 - 1760<br>3 - 1700<br>4 - 1880<br>Avg. - 1795 | 100% |

The plots in all trials were irrigated on the same dates, as follows:
First irrigation —June 22.
Second irrigation —July 24.
Third irrigation —August 8.

In each trial, including Trial 4, which was the control, the seeds were treated with a commercially-available conventional fungicide. In Trial 1, the seeds were treated prior to planting with both a fungicide and Composition C, applied as by spraying. The seeds in Trials 2 and 3 received fungicide treatment only.

It will be apparent upon a review of the data of Table 1, that the plants treated with Composition D in Trials 1, 2 and 3 evidenced a substantial increase in crop yield over those plants grown without such application in Trial 4.

EXAMPLE II

The effect of Composition A on several different varieties of grape was experimentally tested and the results are set forth in Table II below. 160 acres of each variety were treated by the soil application of Composition A and the results of such treatment were compared with the yield of 160 acres of the same variety of grape, located in the same vineyard, but left untreated, to serve as a control. The application of Composition A in each case was in early February, which is a dormant period in the growth cycle of the grapevines.

TABLE II

| VARIETY | 5-YEAR YIELD AVERAGE (TONS/ACRE) | 1983 YIELD | RATE OF APPLICATION COMPOSITION A |
| --- | --- | --- | --- |
| (Treated) Barbera | 8.50 | 9.40 | 1 PINT/ACRE |
| (Control) Barbera | 8.60 | 9.10 | — |
| (Treated) Grenache | 15.90 | 17.20 | 1 QUART/ACRE |
| (Control) Grenache | 16.00 | 10.90 | — |
| (Treated) Chenin Blanc | 10.80 | 9.60 | 1 PINT/ACRE |
| (Control) Chenin Blanc | 10.30 | 7.40 | — |

In Table II, the average yields of grapes in tons per acre for the five-year period preceding the year in which the test was conducted is set forth for both treated and untreated acres. Each variety of grape received a single application. The yield in tons per acre of the treated acres of each variety was greater than that of the controlled acreage of each variety.

EXAMPLE III 160 acres of grapevines of each of the varieties listed in Table III below were treated with Composition C at the rate indicated. Again, each 160 acre tract of grapevines treated was compared with 160 acres of untreated grapevines in the same vineyard and of the same variety, left untreated to serve as a control. The vines of the treated acreage received a single application of Composition C in early February during the dormant period in the vegetative cycle of the vines.

TABLE III

| VARIETY | 5-YEAR YIELD AVERAGE (TONS/ACRE) | 1983 YIELD (TONS/ACRE) | RATE OF APPLICATION COMPOSITION C (COMPOSITION A + B) |
| --- | --- | --- | --- |
| (Treated) Semillon | 8.72 | 10.40 | 1 Quart Composition A + 1 Quart Composition B/Acre |
| (Control) Semillon | 8.40 | 9.40 | — |
| (Treated) Ruby Cabernet | 7.50 | 7.70 | 1 Pint Composition A + 1 Quart Composition B/Acre |
| (Control) Ruby Cabernet | 7.50 | 5.00 | — |
| (Treated) Emerald Riesling | 9.80 | 6.20 | 1 Pint Composition A + 1 Quart Composition B/Acre |
| (Control) Emerald Riesling | 9.70 | 5.50 | — |

As did the application of Composition A, set forth in Table II in Example II, the applications of Composition C, the results of which are set forth immediately above in Table III, provided a greater crop yield per acre than was obtained from the untreated acreage. It was also experimentally observed that the vines of the treated acreage had a much more rapid and voluminous vegetative growth and an earlier date of maturity.

EXAMPLE IV

Olives of the Ascolino and Manzanillo varieties were treated with Composition D and the results of such treatment are set forth in Table IV. The applications of Composition D were made by foliar spraying.

Both the Manzanillo and, to a lesser extent, the Ascolino varieties of olive, are cyclical or alternate in their seasonal bearing of olives. That is, normally, in one of each pair of succeeding years or growing seasons, the trees of each variety will produce at a depressed level relative to the other of such succeeding pair of years. The trees of the control group of each variety produced significantly lower yields of olives in the year in which the test was conducted as compared to the preceeding year, during which none of the trees were treated. The trees each received a single application.

again with no delay in the maturity of the cotton. The yields obtained from the application of Composition D in combination with PIX resulted in significantly larger yields than those using PIX alone. However, it is noted that the yields of the control group were also significantly higher than the groups on which PIX alone was applied.

Thus, it is seen that the present invention provides a process for producing a plant growth modifying composition, and a method for the use thereof, useful in modifying both vegetative and fruiting growth in an-

TABLE IV

| TRIAL | VARIETY | ACRES TREATED | YIELD (TONS/ACRE) IN TEST YEAR | YIELD (TONS/ACRE) PRECEDING YEAR - UNTREATED | TIMING OF APPLICATION |
|---|---|---|---|---|---|
| 1 | Manzanillo | 17 | 2.84 | 7.9 | Post-Harvest (Fall Treatment) |
| 2 | Manzanillo | 11.5 | 1.69 | 7.5 | Spring Treatment |
| 3 | Ascolino | 8 | 6.02 | 7.4 | Spring Treatment |
| 4 | Manzanillo | (Control - 10 acres untreated) | 1.26 | 4.9 | — |
| 5 | Ascolino | (Control - 10 acres untreated) | 3.61 | 7.3 | — |

EXAMPLE V

Composition D was tested on plots of cotton in combination with PIX for comparison of the effects of such application with the yield obtained applying PIX alone, and also with a control field left untreated.

nual and perennial plants and compatible with conventional agriculture methods, materials, and practices.

While the composition and method of the instant invention are described in terms of particular ingredients, and ranges thereof, to be used, it is understood that modifications and variations in the nature and propor-

TABLE V

| TRIAL | VOLUME/ACRE PIX APPLIED | VOLUME/ACRE COMPOSITION D APPLIED | YIELD (LBS. SEED COTTON/ACRE) (AVG. 4 REPLICATIONS) | TIME OF APPLICATION |
|---|---|---|---|---|
| 1 | 1 Pint | 2 Quarts | 3597 | First Bloom |
| 2 | 1 Pint | 0 | 3382 | First Bloom |
| 3 (Control) | 0 | 0 | 3382 | — |

Each trial was replicated four times and the yield of seed cotton per acre for each trial represents the average of the yields of the four replications.

The cotton plants treated with the combination of PIX and Composition D were approximately six inches taller, on the average, than the plants treated solely with PIX. No delay in maturity of the cotton was observed.

EXAMPLE VI

Varying rates of application of PIX and PIX plus Composition D were tested against control plots of cotton to determine the relative effects on the yields of cotton plants so treated. The results are summarized in Table VI below.

tions of the ingredients may be made without departing from the spirit and scope of the invention, which is not to be limited to the illustrative details disclosed.

Having described my invention, what I claim as new and desire to secure by Letters Patent is:

1. A process for preparing a liquid composition for modifying plant growth comprising the steps of heating an aqueous reaction medium to a temperature in the range of from about 170° F. to about 225° F.; adding leonardite ore to the aqueous reaction medium; adding at least one member of the group consisting of the sodium, potassium, ammonium, copper, iron, magnesium, manganese, zinc, calcium, lithium, rubidium and cesium salts of gluconic acid, glucoheptoic acid, citric acid,

TABLE VI

| TRIAL | VOLUME PIX PER ACRE | VOLUME COMPOSITION D PER ACRE | AVERAGE YIELD, LBS. OF SEED COTTON PER ACRE (4 REPLICATIONS) |
|---|---|---|---|
| 1 | ¾ Pints | 0 | 3413 |
| 2 | ½ Pints | 0 | 3506 |
| 3 | ¾ Pints | 5 Pints | 3610 |
| 4 | ½ Pints | 5 Pints | 3733 |
| 5 | 0 | 0 | 3642 |

Each trial was replicated four times and the yield of seed cotton per acre for each trial represents the average yield of the four replications.

Again, the growth pattern of the plants treated with Composition D in combination with PIX showed an average increase in height of approximately six inches, tartaric acid, tartronic acid, galactaric acid, glucaric acid, glutaric acid, and glutamic acid to the reaction medium; mixing the aqueous medium for a period of time sufficient to permit reaction thereamong; and permitting the reacted mixture to settle to effect a separation thereof into the liquid composition for modifying plant growth and a solid phase of excess solid matter.

2. The process of claim 1 further comprising adjusting the pH of the liquid composition to at least as high as about 12.5 by the addition of a base thereto.

3. The composition produced in accordance with the process of claim 2.

4. The process of claim 2 wherein the base is selected from the group consisting of sodium hydroxide and potassium hydroxide.

5. The composition produced in accordance with the process of claim 4.

6. The process of claim 2 further comprising combining the liquid composition with a member selected from the group consisting of N,N-dimethyl piperidinium chloride and 2-chloroethyl trimethyl ammonium chloride.

7. The composition produced in accordance with the process of claim 6.

8. The process of claim 1 further comprising combining the liquid composition with a second liquid composition prepared by the process of reacting leonardite ore in a heated aqueous medium with a member selected from the group consisting of potassium hydroxide and sodium hydroxide; adding hydrogen peroxide to the aqueous medium; and removing excess solid matter to yield the second liquid composition.

9. The composition produced in accordance with the process of claim 8.

10. A process for preparing a liquid composition for modifying plant growth comprising heating an aqueous reaction medium to a temperature in the range of from about 170° F. to about 225° F.; adding leonardite ore to the aqueous medium; adding at least one member of the group consisting of sodium glucamine, potassium glucamine, ammonium glucamine, copper glucamine, ferrous glucamine, magnesium glucamine, manganese glucamine, zinc glucamine, calcium glucamine, lithium glucamine, rubidium glucamine, and cesium glucamine to the reaction medium; mixing the reaction medium for a period of time sufficient to permit reaction thereamong; and permitting the reacted mixture to settle to effect a separation thereof into the liquid composition for modifying plant growth and a solid phase of excess solid matter.

11. The process of claim 10 further comprising combining the liquid composition with a second liquid composition prepared by the process of reacting leonardite ore in a heated aqueous medium with a member selected from the group consisting of potassium hydroxide and sodium hydroxide; adding hydrogen peroxide to the aqueous medium; and removing excess solid matter to yield the second liquid composition.

12. The composition produced in accordance with the process of claim 11.

13. The process of claim 10 further comprising the steps of separating the liquid composition form the excess solid matter and combining the liquid composition with a second liquid composition prepared by the process of heating a quantity of water to a temperature in the range of from about 180° F. to about 200° F.; adding leonardite ore to the water to provide a reaction mixture; blending the reaction mixture; introducing a base selected from the group consisting of potassium hydroxide and sodium hydroxide into the blended reaction mixture; introducing hydrogen peroxide into the reaction mixture; permitting the reaction mixture to settle; and removing excess solid matter, with the remaining liquid being the second liquid composition.

14. The composition produced in accordance with the process of claim 13.

15. The process of claim 10 further comprising combining the liquid composition with a member selected from the group consisting of N,N-dimethyl piperidinium chloride and 2-Chloroethyl trimethyl ammonium chloride.

16. The composition produced in accordance with the process of claim 15.

17. The process of claim 10 further comprising the step of adjusting the pH of the liquid composition to at least as high as about 12.5.

18. The composition produced in accordance with the process of claim 17.

19. A method of producing a liquid composition for modifying plant growth comprising the steps of heating an aqueous reaction medium to a temperature in the range of from about 170° F. to about 225° F.; adding leonardite ore to the aqueous medium; adding at least one member selected from the group consisting of the sodium, potassium, ammonium, copper, iron, magnesium, manganese, zinc, calcim, lithium, rubidium and cesium salts of ethylene diamine tetraacetic acid, hydroxyethylene diamine triacetic acid, diethylene triamine pentaacetic acid, nitrillo triacetic acid, and ethanol diglycine to the reaction medium; mixing the aqueous medium for a period of time sufficient to permit reaction thereamong; and permitting the reacted mixture to settle to effect a separation thereof into a liquid composition for modifying plant growth and a solid phase of excess solid matter.

20. The process of claim 19 further comprising the steps of separating the liquid composition from the excess solid matter and combining the liquid composition with a second liquid composition prepared by the process of heating a quantity of water to a temperature in the range of from about 180° F. to about 200° F.; adding leonardite ore to the water to provide a reaction mixture; blending the reaction mixture; introducing a base selected from the group consisting of potassium hydroxide and sodium hydroxide into the blended reaction mixture; introducing hydrogen peroxide into the reaction mixture; permitting the reaction mixture to settle; and removing excess solid matter, with the remaining liquid being the second liquid composition.

21. The process of claim 19 further comprising combining the liquid composition with a second liquid composition prepared by the process of reacting leonardite ore in a heated aqueous medium with a member selected from the group consisting of potassium hydroxide and sodium hydroxide; adding hydrogen peroxide to the aqueous medium; and removing excess solid matter to yield the second liquid composition.

22. The composition produced in accordance with the process of claim 21.

23. The process of claim 19 further comprising combining the liquid composition with a member selected from the group consisting of N,N-dimethyl piperidinium chloride and 2-Chloroethyl trimethyl ammonium chloride.

24. The composition produced in accordance with the process of claim 23.

\* \* \* \* \*